United States Patent [19]

Bukowick

[11] 4,115,093

[45] Sep. 19, 1978

[54] CERTAIN OXIMINYL ALLOPHANATES AND THEIR USE AS HERBICIDES

[75] Inventor: Peter Anthony Bukowick, New Castle, Del.

[73] Assignee: Hercules Incorporated, Wilmington, Del.

[21] Appl. No.: 765,176

[22] Filed: Feb. 3, 1977

Related U.S. Application Data

[60] Division of Ser. No. 626,524, Oct. 28, 1975, Pat. No. 4,030,912, which is a continuation of Ser. No. 350,218, Apr. 11, 1973, Pat. No. 3,957,867.

[51] Int. Cl.$^2$ ............................................. A01N 9/00
[52] U.S. Cl. ............................................................ 71/88
[58] Field of Search ................................... 71/88, 121

[56] References Cited

U.S. PATENT DOCUMENTS

| | | | |
|---|---|---|---|
| 2,804,381 | 8/1957 | Garman et al. | 71/88 |
| 2,929,702 | 3/1960 | Speziale | 71/88 |
| 3,063,823 | 11/1962 | Kuhle et al. | 71/121 |
| 3,483,246 | 12/1969 | Kaufman | 71/88 |

FOREIGN PATENT DOCUMENTS 1,032,595 12/1956 Fed. Rep. of Germany ............ 71/111
4,643,218 12/1971 Japan ........................................... 71/88

*Primary Examiner*—Glennon H. Hollrah
*Attorney, Agent, or Firm*—George H. Hopkins

[57] ABSTRACT

Disclosed are novel compounds of the formula

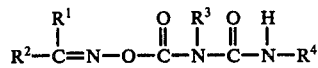

in which when $R^1$ and $R^2$ are taken separately, $R^1$ is selected independently from the group consisting of hydrogen and $C_1$–$C_7$ alkyl and $R^2$ is selected independently from the group consisting of $C_1$–$C_7$ alkyl, phenyl and 2-furanyl, and, when taken together with the carbon atom to which they are attached $R^1$ and $R^2$ form a $C_3$–$C_8$ cycloalkyl group; $R^3$ is selected from the group consisting of $C_1$–$C_7$ alkyl, allyl, phenyl, 3-halophenyl and 3,4-dihalophenyl; and $R^4$ is selected from the group consisting of $C_1$–$C_7$ alkyl, allyl, cyclohexyl, phenyl, halophenyl, tolyl, anisolyl, nitrophenyl, 3,4-dihalophenyl, 1-naphthyl, p-toluene sulfonyl, trihalomethylphenyl and 2,6-dinitro-4-trihalomethylphenyl. These compounds have herbicidal activity.

6 Claims, No Drawings

CERTAIN OXIMINYL ALLOPHANATES AND THEIR USE AS HERBICIDES

The application is a division of the application, Ser. No. 626,524, filed Oct. 28, 1975, as a division of the application, Ser. No. 350,218, filed Apr. 11, 1973. U.S. Pat. No. 3,957,867 was granted on the Ser. No. 350,218 application, while U.S. Pat. No. 4,030,912 was granted on the Ser. No. 626,524 application.

This invention is in the chemical arts. It relates to that part of organic chemistry having to do with allophanates. It also relates to herbicides.

The allophanates of this invention are oximinyl allophanates. They are represented by the general structural formula:

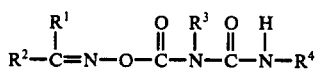

in which when $R^1$ and $R^2$ are taken separately, $R^1$ is selected independently from the group consisting of hydrogen and $C_1$–$C_7$ alkyl and $R^2$ is selected independently from the group consisting of $C_1$–$C_7$ alkyl, phenyl and 2-furanyl, and, when taken together with the carbon atom to which they are attached $R^1$ and $R^2$ form a $C_3$–$C_8$ cycloalkyl group; $R^3$ is selected from the group consisting of $C_1$–$C_7$ alkyl, allyl, phenyl, 3-halophenyl and 3,4-dihalophenyl; and $R^4$ is selected from the group consisting of $C_1$–$C_7$ alkyl, allyl, cyclohexyl, phenyl, halophenyl, tolyl, anisolyl, nitrophenyl, 3,4-dihalophenyl, 1-naphthyl, p-toluenesulfonyl, trihalomethylphenyl and 2,6-dinitro-4-trihalomethylphenyl. Examples of $C_1$–$C_7$ alkyl include methyl, ethyl, propyl, isopropyl, butyl, sec. butyl, t-butyl and the like. Examples of $C_3$–$C_8$ cycloalkyl include cyclopropyl, cyclobutyl, cyclopentyl, cyclohexyl and the like. Examples of specific compounds of this invention include:

Isobutyraldoximinyl-2-methyl-4-ethyl allophanate
Isobutyraldoximinyl-2-methyl-4-(t-butyl) allophanate
Isobutyraldoximinyl-2-methyl-4-(3,4-dichlorophenyl)allophanate
Isobutyraldoximinyl-2-methyl-4-(1-naphthyl)allophanate
Isobutyraldoximinyl-2-(n-propyl)-4-methyl allophanate
Isobutyraldoximinyl-2,4-di(n-propyl)allophanate
Isobutyraldoximinyl-2-(n-propyl)-4-(t-butyl)allophanate
Isobutyraldoximinyl-2-(n-propyl)-4-phenyl allophanate
Isobutyraldoximinyl-2-(n-propyl)-4-(3,4-dichlorophenyl)allophanate
Isobutyraldoximinyl-2-(n-propyl)-4-(1-naphthyl)allophanate
Isobutyraldoximinyl-2-phenyl-4-methyl allophanate
Isobutyraldoximinyl-2-phenyl-4-allyl allophanate
Isobutyraldoximinyl-2-phenyl-4-(n-butyl)allophanate
Isobutyraldoximinyl-2,4-diphenyl allophanate
Isobutyraldoximinyl-2-phenyl-4-(p-chlorophenyl)allophanate
Isobutyraldoximinyl-2-phenyl-4-(3,4-dichlorophenyl)allophanate
Isobutyraldoximinyl-2-(3,4-dichlorophenyl)-4-isopropyl allophanate
Isobutyraldoximinyl-2-(3,4-dichlorophenyl)-4-(n-butyl)allophanate
Isobutyraldoximinyl-2-(3,4-dichlorophenyl)-4-phenyl allophanate
Isobutyraldoximinyl-2-(3,4-dichlorophenyl)-4-(p-chlorophenyl) allophanate
Isobutyraldoximinyl-2-(3,4-dichlorophenyl)-4-(m-tolyl)allophanate
Benzaldoximinyl-2-methyl-4-ethyl allophanate
Benzaldoximinyl-2-methyl-4-allyl allophanate
Benzaldoximinyl-2-methyl-4-(n-butyl)allophanate
Benzaldoximinyl-2-methyl-4-phenyl allophanate
Benzaldoximinyl-2-methyl-4-(3-chlorophenyl)allophanate
Benzaldoximinyl-2-methyl-4-(4-chlorophenyl)allophanate
Benzaldoximinyl-2-allyl-4-methyl allophanate
Benzaldoximinyl-2,4-diallyl allophanate
Benzaldoximinyl-2-allyl-4-(n-butyl)allophanate
Benzaldoximinyl-2-allyl-4-isopropyl allophanate
Benzaldoximinyl-2-allyl-4-phenyl allophanate
Benzaldoximinyl-2-allyl-4-(3-chlorophenyl)allophanate
Benzaldoximinyl-2-allyl-4-(4-chlorophenyl)allophanate
Benzaldoximinyl-2-allyl-4-(3,4-dichlorophenyl)allophanate
Benzaldoximinyl-2-allyl-4-(4-methoxyphenyl)allophanate
Benzaldoximinyl-2-allyl-4-(p-toluenesulfonyl)allophanate
Benzaldoximinyl-2-phenyl-4-methyl allophanate
Benzaldoximinyl-2-phenyl-4-ethyl allophanate
Benzaldoximinyl-2-phenyl-4-allyl allophanate
Benzaldoximinyl-2-phenyl-4-(n-propyl)allophanate
Benzaldoximinyl-2-phenyl-4-(n-butyl)allophanate
Benzaldoximinyl-2,4-diphenyl allophanate
Benzaldoximinyl-2-phenyl-4-(3-chlorophenyl)allophanate
Benzaldoximinyl-2-phenyl-4-(4-chlorophenyl)allophanate
Benzaldoximinyl-2-phenyl-4-(3,4-dichlorophenyl)allophanate
Benzaldoximinyl-2-(3-chlorophenyl)-4-methyl allophanate
Benzaldoximinyl-2-(3-chlorophenyl)-4-ethyl allophanate
Benzaldoximinyl-2-(3-chlorophenyl)-4-allyl allophanate
Benzaldoximinyl-2-(3-chlorophenyl)-4-(n-butyl)allophanate
Benzaldoximinyl-2-(3-chlorophenyl)-4-phenyl allophanate
Benzaldoximinyl-2,4-di-(3-chlorophenyl)allophanate
Benzaldoximinyl-2-(3-chlorophenyl)-4-(4-chlorophenyl)allophanate
Benzaldoximinyl-2-(3-chlorophenyl)-4-(3,4-dichlorophenyl)allophanate
Benzaldoximinyl-2-(3-chlorophenyl)-4-(nitrophenyl)allophanate
Benzaldoximinyl-2-(3,4-dichlorophenyl)-4-methyl allophanate
Benzaldoximinyl-2,4-di-(3,4-dichlorophenyl)allophanate
2-Furaldoximinyl-2,4-dimethyl allophanate
2-Furaldoximinyl-2-methyl-4-ethyl allophanate
2-Furaldoximinyl-2-methyl-4-allyl allophanate
2-Furaldoximinyl-2-methyl-4-(n-propyl)allophanate
2-Furaldoximinyl-2-methyl-4-(n-butyl)allophanate
2-Furaldoximinyl-2-methyl-4-phenyl allophanate
2-Furaldoximinyl-2-methyl-4-(3-chlorophenyl)allophanate
2-Furaldoximinyl-2-methyl-4-(4-chlorophenyl)allophanate 2-Furaldoximinyl-2-methyl-4-(4-methoxyphenyl)allophanate
2-Furaldoximinyl-2-methyl-4-(4-methylphenyl)allophanate
2-Furaldoximinyl-2-phenyl-4-ethyl allophanate
2-Furaldoximinyl-2-phenyl-4-allyl allophanate
2-Furaldoximinyl-2,4-diphenyl allophanate
2-Furaldoximinyl-2-phenyl-4-(3-chlorophenyl)allophanate
2-Furaldoximinyl-2-phenyl-4-(4-chlorophenyl)allophanate
2-Furaldoximinyl-2-(3-chlorophenyl)-4-methyl allophanate
2-Furaldoximinyl-2-(3-chlorophenyl)-4-ethyl allophanate
2-Furaldoximinyl-2-(3-chlorophenyl)-4-allyl allophanate
2-Furaldoximinyl-2-(3-chlorophenyl)-4-phenyl allophanate
2-Furaldoximinyl-2,4-bis-(3-chlorophenyl)allophanate
2-Furaldoximinyl-2-(3-chlorophenyl)-4-(4-chlorophenyl)allophanate
Acetone oximinyl-2,4-dimethyl allophanate
Acetone oximinyl-2-methyl-4-allyl allophanate
Acetone oximinyl-2-methyl-4-phenyl allophanate
Acetone oximinyl-2-methyl-4-(3-chlorophenyl)allophanate
Acetone oximinyl-2-methyl-4-(4-chlorophenyl)allophanate
Acetone oximinyl-2-methyl-4-(3,4-dichlorophenyl)allophanate
Acetone oximinyl-2-methyl-4-(4-methoxyphenyl)allophanate
Acetone oximinyl-2-methyl-4-(nitrophenyl)allophanate
Acetone oximinyl-2-methyl-4-(3-trifluoromethylphenyl)allophanate
Acetone oximinyl-2-allyl-4-methyl allophanate
Acetone oximinyl-2,4-diallyl allophanate
Acetone oximinyl-2-allyl-4-cyclohexyl allophanate
Acetone oximinyl-2-allyl-4-(n-butyl)allophanate
Acetone oximinyl-2-allyl-4-phenyl allophanate
Acetone oximinyl-2-allyl-4-(3-chlorophenyl)allophanate
Acetone oximinyl-2-allyl-4-(3,4-dichlorophenyl)allophanate
Acetone oximinyl-2-allyl-4-(toluenesulfonyl)allophanate
Acetone oximinyl-2-phenyl-4-methyl allophanate
Acetone oximinyl-2-phenyl-4-allyl allophanate
Acetone oximinyl-2-phenyl-4-isopropyl allophanate
Acetone oximinyl-2-phenyl-4-(n-butyl)allophanate
Acetone oximinyl-2,4-diphenyl allophanate
Acetone oximinyl-2-phenyl-4-(3-chlorophenyl)allophanate
Acetone oximinyl-2-phenyl-4-(3,4-dichlorophenyl)allophanate
Acetone oximinyl-2-(3-chlorophenyl)-4-methyl allophanate
Acetone oximinyl-2-(3-chlorophenyl)-4-allyl allophanate
Acetone oximinyl-2-(3-chlorophenyl)-4-(n-butyl)allophanate
Acetone oximinyl-2-(3-chlorophenyl)-4-phenyl allophanate
Acetone oximinyl-di-2,4-(3-chlorophenyl)allophanate
Acetone oximinyl-2-(3-chlorophenyl)-4-(3,4-dichlorophenyl)allophanate
Acetone oximinyl-2-(3-chlorophenyl)-4-(p-toluenesolfonyl)allophanate
Acetone oximinyl-2-(3,4-dichlorophenyl)-4-methyl allophanate
Acetone oximinyl-2,4-di-(3,4-dichlorophenyl)allophanate
2-Butanone oximinyl-2,4-dimethyl allophanate
2-Butanone oximinyl-2-methyl-4-ethyl allophanate
2-Butanone oximinyl-2-methyl-4-allyl allophanate
2-Butanone oximinyl-2-methyl-4-(n-butyl)allophanate
2-Butanone oximinyl-2-methyl-4-phenyl allophanate
2-Butanone oximinyl-2-methyl-4-(m-chlorophenyl)allophanate
2-Butanone oximinyl-2-methyl-4-(3,4-dichlorophenyl)allophanate
2-Butanone oximinyl-2-methyl-4-(o-tolyl)allophanate
2-Butanone oximinyl-2-methyl-4-(m-tolyl)allophanate
2-Butanone oximinyl-2-methyl-4-(p-tolyl)allophanate
2-Butanone oximinyl-2-methyl-4-(1-naphthyl)allophanate
2-Butanone oximinyl-2-methyl-4-(3-trifluoromethylphenyl)allophanate
2-Butanone oximinyl-2-(n-butyl)-4-methyl allophanate
2-Butanone oximinyl-2-(n-butyl)-4-allyl allophanate
2-Butanone oximinyl-2-(n-butyl)-4-ethyl allophanate
2-Butanone oximinyl-2-(n-butyl)-4-isopropyl allophanate
2-Butanone oximinyl-2,4-di-(n-butyl)allophanate
2-Butanone oximinyl-2-(n-butyl)-4-phenyl allophanate
2-Butanone oximinyl-2-(n-butyl)-4-(m-chlorophenyl)allophanate
2-Butanone oximinyl-2-(n-butyl)-4-(3,4-dichlorophenyl)allophanate
2-Butanone oximinyl-2-(n-butyl)-4-(m-tolyl)allophanate
2-Butanone oximinyl-2-(n-butyl)-4-(1-naphthyl)allophanate
2-Butanone oximinyl-2-phenyl-4-methyl allophanate
2-Butanone oximinyl-2-phenyl-4-ethyl allophanate
2-Butanone oximinyl-2-phenyl-4-allyl allophanate
2-Butanone oximinyl-2-phenyl-4-isopropyl allophanate
2-Butanone oximinyl-2-phenyl-4-(n-butyl)allophanate
2-Butanone oximinyl-2,4-diphenyl allophanate
2-Butanone oximinyl-2-phenyl-4-(m-chlorophenyl)allophanate
2-Butanone oximinyl-2-phenyl-4-(p-tolyl)allophanate
2-Butanone oximinyl-2-phenyl-4-(1-naphthyl)allophanate
2-Butanone oximinyl-2-phenyl-4-(3,4-dichlorophenyl)allophanate
2-Butanone oximinyl-2-(m-chlorophenyl)-4-methyl allophanate
2-Butanone oximinyl-2-(m-chlorophenyl)-4-(n-butyl)allophanate
2-Butanone oximinyl-2-(m-chlorophenyl)-4-ethyl allophanate
2-Butanone oximinyl-2-(m-chlorophenyl)-4-phenyl allophanate
2-Butanone oximinyl-2,4-di-(m-chlorophenyl)allophanate
2-Butanone oximinyl-2-(m-chlorophenyl)-4-isopropyl allophanate
2-Butanone oximinyl-2-(m-chlorophenyl)-4-(o-tolyl)allophanate
2-Butanone oximinyl-2-(m-chlorophenyl)-4-(1-naphthyl)allophanate
2-Butanone oximinyl-2-(m-chlorophenyl)-4-(t-butyl)allophanate 2-Butanone oximinyl-2-(m-chlorophenyl)-4-(3,4-dichlorophenyl) allophanate
2-Butanone oximinyl-2,4-di(3,4-dichlorophenyl)allophanate
2-Butanone oximinyl-2-(3,4-dichlorophenyl)-4-methyl allophanate
Methyl isobutylketoximinyl-2,4-dimethyl allophanate
Methyl isobutylketoximinyl-2-methyl-4-isopropyl allophanate
Methyl isobutylketoximinyl-2-methyl-4-(n-butyl)allophanate
Methyl isobutylketoximinyl-2-methyl-4-phenyl allophanate
Methyl isobutylketoximinyl-2-methyl-4-(p-chlorophenyl)allophanate
Methyl isobutylketoximinyl-2-methyl-4-(3,4-dichlorophenyl)allophanate
Methyl isobutylketoximinyl-2-methyl-4-(1-naphthyl)allophanate
Methyl isobutylketoximinyl-2-(n-propyl)-4-methyl allophanate
Methyl isobutylketoximinyl-2-(n-propyl)-4-isopropyl allophanate
Methyl isobutylketoximinyl-2-(n-propyl)-4-(n-butyl)allophanate
Methyl isobutylketoximinyl-2-(n-propyl)-4-phenyl allophanate
Methyl isobutylketoximinyl-2-(n-propyl)-4-(p-chlorophenyl)allophanate
Methyl isobutylketoximinyl-2-(n-propyl)-4-(3,4-dichlorophenyl) allophanate Methyl isobutylketoximinyl-2-(n-propyl)-4-(1-naphthyl)allophanate
Methyl isobutylketoximinyl-2-phenyl-4-methyl allophanate
Methyl isobutylketoximinyl-2-phenyl-4-isopropyl allophanate
Methyl isobutylketoximinyl-2-phenyl-4-(n-butyl)allophanate
Methyl isobutylketoximinyl-2-phenyl-4-phenyl allophanate
Methyl isobutylketoximinyl-2-phenyl-4-(p-chlorophenyl)allophanate
Methyl isobutylketoximinyl-2-phenyl-4-(1-naphthyl)allophanate
Methyl isobutylketoximinyl-2-phenyl-4-(3,4-dichlorophenyl)allophanate
Methyl isobutylketoximinyl (3,4-dichlorophenyl)-4-methyl allophanate
Methyl isobutylketoximinyl (3,4-dichlorophenyl)-4-isopropyl allophanate
Methyl isobutylketoximinyl (3,4-dichlorophenyl)-4-(n-butyl) allophanate
Methyl isobutylketoximinyl (3,4-dichlorophenyl)-4-phenyl allophanate
Methyl isobutylketoximinyl (3,4-dichlorophenyl)-4-(p-chlorophenyl) allophanate
Methyl isobutylketoximinyl (3,4-dichlorophenyl)-4-(1-naphthyl) allophanate
Acetophenone oximinyl-2,4-dimethyl allophanate
Acetophenone oximinyl-2-methyl-4-ethyl allophanate
Acetophenone oximinyl-2-methyl-4-allyl allophanate
Acetophenone oximinyl-2-methyl-4-isopropyl allophanate
Acetophenone oximinyl-2-methyl-4-(n-butyl)allophanate
Acetophenone oximinyl-2-methyl-4-phenyl allophanate
Acetophenone oximinyl-2-methyl-4-(3,4-dichlorophenyl)allophanate
Acetophenone oximinyl-2-methyl-4-(m-tolyl)allophanate
Acetophenone oximinyl-2-methyl-4-(1-naphthyl)allophanate
Acetophenone oximinyl-2-methyl-4-(3-trifluoromethylphenyl)allophanate
Acetophenone oximinyl-2-(n-butyl)-4-methyl allophanate
Acetophenone oximinyl-2-(n-butyl)-4-ethyl allophanate
Acetophenone oximinyl-2-(n-butyl)-4-allyl allophanate
Acetophenone oximinyl-2-(n-butyl)-4-isopropyl allophanate
Acetophenone oximinyl-2,4-di-(n-butyl)allophanate
Acetophenone oximinyl-2-(n-butyl)-4-phenyl allophanate
Acetophenone oximinyl-2-(n-butyl)-4-(3,4-dichlorophenyl)allophanate
Acetophenone oximinyl-2-(n-butyl)-4-(m-chlorophenyl)allophanate
Acetophenone oximinyl-2-(n-butyl)-4-(m-tolyl)allophanate
Acetophenone oximinyl-2-(n-butyl)-4-(1-naphthyl)allophanate
Acetophenone oximinyl-2-phenyl-4-methyl allophanate
Acetophenone oximinyl-2-phenyl-4-ethyl allophanate
Acetophenone oximinyl-2-phenyl-4-allyl allophanate
Acetophenone oximinyl-2-phenyl-4-isopropyl allophanate
Acetophenone oximinyl-2-phenyl-4-(n-butyl)allophanate
Acetophenone oximinyl-2,4-diphenyl allophanate
Acetophenone oximinyl-2-phenyl-4-(m-chlorophenyl)allophanate
Acetophenone oximinyl-2-phenyl-4-(3,4-dichlorophenyl)allophanate
Acetophenone oximinyl-2-phenyl-4-(m-tolyl)allophanate
Acetophenone oximinyl-2-phenyl-4-(1-naphthyl)allophanate
Acetophenone oximinyl-2-(m-chlorophenyl)-4-methyl allophanate
Acetophenone oximinyl-2-(m-chlorophenyl)-4-ethyl allophanate
Acetophenone oximinyl-2-(m-chlorophenyl)-4-allyl allophanate
Acetophenone oximinyl-2-(m-chlorophenyl)-4-(n-propyl)allophanate
Acetophenone oximinyl-2-(m-chlorophenyl)-4-(n-butyl)allophanate
Acetophenone oximinyl-2-(m-chlorophenyl)-4-(m-tolyl)allophanate
Acetophenone oximinyl-2-(m-chlorophenyl)-4-(1-naphthyl)allophanate
Acetophenone oximinyl-2-(3,4-dichlorophenyl)-4-methyl allophanate Acetophenone oximinyl-2,4-di-(3,4-dichlorophenyl)allophanate
Cyclohexanone oximinyl-2,4-dimethyl allophanate
Cyclohexanone oximinyl-2-methyl-4-ethyl allophanate
Cyclohexanone oximinyl-2-methyl-4-allyl allophanate
Cyclohexanone oximinyl-2-methyl-4-(n-propyl)allophanate
Cyclohexanone oximinyl-2-methyl-4-(n-butyl)allophanate
Cyclohexanone oximinyl-2-methyl-4-phenyl allophanate
Cyclohexanone oximinyl-2-methyl-4-(4-chlorophenyl)allophanate Cyclohexanone oximinyl-2-methyl-4-(3-chlorophenyl)allophanate
Cyclohexanone oximinyl-2-methyl-4-(4-methoxyphenyl)allophanate
Cyclohexanone oximinyl-2-phenyl-4-methyl allophanate
Cyclohexanone oximinyl-2-phenyl-4-allyl allophanate
Cyclohexanone oximinyl-2-phenyl-4-isopropyl allophanate
Cyclohexanone oximinyl-2-phenyl-4-(n-butyl)allophanate
Cyclohexanone oximinyl-2,4-diphenyl allophanate
Cyclohexanone oximinyl-2-phenyl-4-(3-chlorophenyl)allophanate
Cyclohexanone oximinyl-2-phenyl-4-(4-chlorophenyl)allophanate
Cyclohexanone oximinyl-2-phenyl-4-(3,4-dichlorophenyl)allophanate
Cyclohexanone oximinyl-2-phenyl-4-(o-tolyl)allophanate
Cyclohexanone oximinyl-2-phenyl-4-(3-methoxyphenyl)allophanate
Cyclohexanone oximinyl-2-phenyl-4-(3-nitrophenyl)allophanate Each oximinyl allophanate of this invention is made by reacting an oximinyl carbamate of the formula $$R^2-\underset{\underset{R^1}{|}}{C}=N-O-\underset{\underset{}{\overset{\overset{O}{\|}}{}}}{C}-\underset{\underset{}{\overset{\overset{H}{|}}{}}}{N}-R^3$$

with an isocyanate of the formula $R^4N{=}C{=}O$. Reaction is effected with a catalyst such as, for example, lead naphthenate, cobalt naphthenate, and the like. Preferably, the reaction is effected in an inert liquid reaction medium such as, for example, benzene, dioxane, acetonitrile, acetone, dimethylformamide and other inert solvents. The reaction temperature is from about 25° C. to about 110° C., preferably in the range of from about 55° C. to about 100° C.

The precurser oxime carbamate for the oximinyl allophanates of this invention is made by carbamoylating an oxime of the formula $$R^2-\underset{\underset{R^1}{|}}{C}=N-OH$$

with an isocyanate of the formula $R^3N{=}C{=}O$ in the presence of a basic catalyst such as, for example, triethylamine.

Each oximinyl allophanate of this invention is also made by reacting a urea compound with phosgene to produce an allophanyl chloride and then displacing the labile chloride of the allophanyl chloride by reaction with an oxime. The reactions are represented by the following equations:

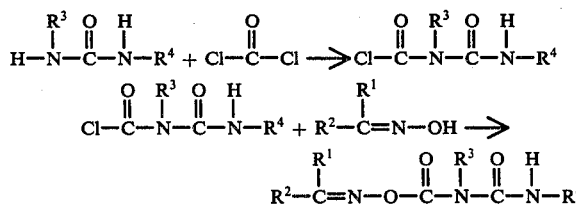

The initial step of the reaction, i.e., the reaction of the urea compound with phosgene, preferably is carried out at atmospheric pressure in an inert liquid reaction medium such as, for example, benzene. No catalyst is necessary. The reaction temperature is in the range of from about 0° C. to about 100° C.

The displacement of the labile chloride of the allophanyl chloride with an oxime takes place preferably in an inert liquid reaction medium such as, for example, benzene and toluene. A sequestering agent can be present to remove the hydrogen chloride and force the reaction to completion. Examples of such sequestering agents are tertiary amines such as, for example, triethylamine. The reaction temperature for this step is preferably between about 25° C. and about 80° C.

The oximinyl allophanates of this invention in general are viscous liquids at 20°-25° C., although some are crystalline solids at this temperature. In general, the water-solubility of each is less than one gram per liter of water, the acetone-solubility of each is greater than 5 grams per liter of acetone, and the benzene-solubility is greater than 10 grams per liter of benzene.

In general, they are biologically active, being phytotoxic to plants, particularly weeds. Hence, they are useful as herbicides. For herbicidal use, generally the oximinyl allophanates are incorporated into herbicidal compositions.

The herbicidal compositions of this invention comprise an effective quantity of phytotoxic material and application aid material.

The phytotoxic material comprises an oximinyl allophanate of this invention, a mixture of two or more of these oximinyl allophanates or a mixture of at least one of these oximinyl allophanates and another phytotoxic substance.

The application aid material is inert material that facilitates distribution or dispersion of the phytotoxic material. Examples of application aid material include diluents, carriers, extenders, surfactants, spreading agents, sticking agents, wind drift control agents, and the like.

The oximinyl allophanates of this invention can be used in herbicidal compositions dissolved or dispersed in a suitable liquid application aid. The liquid application aid is an inert preferably volatile solvent for the oximinyl allophanate. Watersoluble oximinyl allophanates can be dissolved in water for herbicidal use. Water-insoluble oximinyl allophanates can be dissolved in a suitable solvent, such as, for example, isophorone, cyclohexanone, methyl isobutyl ketone, xylene, and the like, to form herbicidal compositions. The solution of the oximinyl allophanate in the solvent is initially in the form of a concentrate. The concentrate can be used directly as the herbicidal composition or it can be diluted with additional solvent or it can be dispersed in water.

Solutions of the oximinyl allophanates dissolved in suitable solvents and oximinyl allophanates which are themselves liquid can also be impregnated into an inert granular solid carrier to provide solid herbicidal compositions. Examples of the inert granular carrier include attaclay, corn cobs, vermiculite, walnut hulls, and almost any granular mineral or organic material of desired particle size.

The solid oximinyl allophanates of this invention can be used in herbicidal compositions along with a finely divided inert solid application aid.

The solid oximinyl allophanates can be coated onto a granular inert carrier which has been admixed with an adhesive or sticker, such as, for example, water, oils, alcohols, glycols, aqueous gums, waxes, and the like, to form a wettable powder or ground powder. Examples of inert granular carriers include attaclay, corn cobs, vermiculite, walnut hulls and almost any other granular mineral or organic material of desired particle size.

The oximinyl allophanates of this invention can be employed according to other known methods of herbicidal application.

The best mode now contemplated of carrying out this invention is illustrated by the following working examples of various aspects of this invention, including specific embodiments. This invention is not limited to these specific embodiments. In these examples, unless otherwise expressly indicated, all percentages are by weight, all parts by weight are represented by "w", all parts by volume are represented by "v" and w is to v as the kilogram is to the liter.

EXAMPLE 1

This example illustrates the preparation of acetone oximinyl-2-methyl-4-phenyl allophanate by reacting acetone oximinyl (N-methyl) carbamate with phenyl isocyanate.

A solution of 250 w of acetone oximinyl (N-methyl) carbamate, 2000 v of dry benzene, 5.6 v of 24% lead naphthenate in mineral oil and 230 w of phenyl isocyanate is heated at reflux for 6 hours. The solution is then cooled and concentrated. The residual solid is washed on a filter with ice-cold ether and then thoroughly dried. Typically 227 w of a white solid having a melting point of 118° C. is obtained. Thin layer chromatography (using 90% benzene, 8% acetone, 2% isopropanol) of the product typically reveals a single spot, $R_f$ 0.50. The nuclear resonance magnetic spectrum ($CDCl_3$) typically is $\delta$ 2.04 [d,6,($CH_3$)$_2$—C], 3.32 (s, 3,N—$CH_3$), 7.0–7.7 (m,$C_6H_5$-), 8.34 (s,1,N-H). Mass spectroscopy reveals a parent peak at m/e 249. [The calculated molecular weight of acetone oximinyl-2-methyl-4-phenyl allophanate is 249.]

EXAMPLE 2

This example illustrates the preparation of acetone oxime-2-methyl-4-phenyl allophanate by the reaction of 1-methyl-3-phenyl urea with phosgene followed by the reaction of the resulting 2-methyl-4-phenyl allophanyl cnloride with acetone oxime.

A mixture of 145 w of 1-methyl-3-phenyl urea and 1000 v of dry benzene is cooled to 10° C. A 12.5% phosgene in benzene solution is then added slowly to the cooled mixture with stirring. The resulting mixture is stirred at ambient temperature for 1.5 hours then at reflux for 2.5 hours. The mixture is cooled and the solids are removed by filtration. A small sample of the filtrate is removed, concentrated and then analyzed for nitrogen content. The analysis typically shows N = 13.6. (Calculated analysis for 2-methyl-4-phenyl allophanyl chloride is N = 13.2%.)

The remainder of the filtrate solution is treated with 68.6 w of acetone oxime. A solution of 95 w triethylamine and 100 v dry benzene is added over a period of 75 minutes while the solution is stirred. Stirring is continued at room temperature for 2 hours and then at reflux for ½ hours. The solution is cooled and the solids are filtered and washed with 150 v benzene. The combined filtrate and wash are washed with two 380 v portions of 5% HCl, dried over magnesium sulfate and concentrated. Typically an orange solid residue is obtained, which when washed with ice-cold ether and dried yields a white solid having a melting point of 119°–121° C.

EXAMPLE 3

This example illustrates the preparation of isobutyraldoximinyl 2-methyl-4-(3,4-dichlorophenyl)allophanate by the reaction of isobutyraldoximinyl(N-methyl)carbamate with 3,4-dichlorophenyl isocyanate.

A solution of 5 w isobutyraldoximinyl (N-methyl) carbamate, 50 v dry dioxane, 8 drops of lead naphthenate and 5.9 w of 3,4-dichlorophenyl isocyanate is heated at reflux for 2 hours. The reaction mixture is then cooled and the solids are removed by filtration. The filtrate is concentrated typically to produce an oily residue (6.1 w). The infrared spectrum of the residue typically has all the bands expected from isobutyraldoximinyl 2-methyl-4-(3,4-dichlorophenyl)allophanate. The analysis for nitrogen content of the oily residue typically shows N = 10.5 (calculated analysis for isobutyraldoximinyl 2-methyl-4-(3,4-dichlorophenyl)allophanate = 12.6.)

EXAMPLE 4

This example illustrates the preparation of isobutyraldoximinyl-2-methyl-4-(3,4-dichlorophenyl)allophanate by the reaction of 1-methyl-3-(3,4-dichlorophenyl) urea with phosgene followed by reaction of the resulting allophanyl chloride with isobutyraldoximine.

A mixture of 14 w 1-methyl-3-(3,4-dichlorophenyl) urea and 100 v dry benzene is cooled and stirred. A 12.5% phosgene in benzene solution is added dropwise over a period of about 1 hour. The resultant mixture is stirred at 25°–30° C. for 18 hours then at reflux for 3 hours. The mixture is then cooled, solids are removed by filtration and the filtrate is concentrated. Typically the residue comprises a tacky, white solid consisting essentially of 2-methyl-4-(3,4-dichlorophenyl)allophanyl chloride.

8.5 w of the allophanyl chloride is stirred with 50 v dry benzene and 2.61 w isobutyraldoxime. A solution of 3 w of triethylamine and 5 w of dry benzene is added. The mixture is stirred at 25°–30° C. for 1 hour then at reflux for ½ hour. The mixture is cooled, the solids are removed by filtration and then washed with dry benzene. The combined filtrate and wash are then washed with 5% HCl. The solids which are formed at this point are then removed by filtration. The organic fraction is dried and concentrated. Typically the residue comprises a brown resin which consists essentially of isobutyraldoximinyl-2-methyl-4-(3,4-dichlorophenyl)allophanate (4.4 w). The residue is analyzed for nitrogen content. The analysis typically shows N = 11.5. (Calculated analysis, N = 12.6.)

The herbicidal activities of the oximinyl allophanates of this invention are illustrated by actual test date summarized in Tables 1 and 2, obtained under standard test conditions with representative oximinyl allophanates made according to the procedures of the foregoing examples.

In each case a concentrate was made from a sample of the oximinyl allophanate by dissolving it in acetone and then adding a commercially available emulsifier which is a blend of a polyoxyethylene (20) sorbitan monooleate in which the oxyethylene content is about 20 mole percent, with mono- and di-glycerides of fatforming fatty acids and an antioxidant mixture consisting essentially of butylated hydroxy anisol, butylated hydroxy toluene, citric acid and propylene glycol. The liquid concentrate was then admixed with water to form an aqueous emulsion with the allophanate at the desired concentration, and the resulting emulsion was then applied in pre-emergence and post-emergence tests.

In the pre-emergence tests seeded pots with seeds of plants identified in Table 1 were sprayed uniformly under a spray of the emulsion sufficient to give a coverage of the allophanate at the indicated pounds per acre of allophanate under test. The extent of plant growth injury was observed after a period of time sufficient for germination and growth of seed and compared to unsprayed seeded pots. The extent of growth and injury was graded from no effect to no growth or complete injury on a scale from 0 to 10.

For post-emergence tests the seeded pots were held under moist growing conditions until the seedlings had reached the first true leaf stage and then the foliage was sprayed with the emulsion sufficiently to give a coverage of the indicated pounds per acre of product under test. After a period of time sufficient for further growth, the extent of plant injury and mortality was determined using the same grading system as above. The results are shown in Table 2.

The oximinyl allophanates of this invention exhibit higher herbicidal activity than the corresponding oximinyl carbamates. The pre-emergence and post-emergence herbicidal activities of certain oximinyl allophanates and the corresponding oximinyl carbamates were determined by the herbicidal test methods described above. Tables 3, 4 and 5 show the comparison between these herbicidal activities.

Various features, advantages and specific embodiments of this invention will be readily apparent to those exercising ordinary skill in the art after reading the foregoing disclosures. Such specific embodiments are within the scope of the claimed subject matter unless expressly indicated otherwise. Moreover, while specific embodiments of this invention have been described in considerable detail, variations and modifications of them can be effected without departing from the spirit and scope of the invention as disclosed and claimed.

The terminology "consisting essentially of" as used in the specification (disclosure and claims) excludes any unrecited substance at a concentration sufficient to substantially adversely affect the essential properties and characteristics of the composition being defined, while permitting the presence of one or more unrecited substances at concentrations insufficient to substantially adversely affect said essential properties and characteristics.

TABLE 1

| Compound | Rate lb./Acre | Cotton | Wheat | Soybeans | Crabgrass | Mustard | Morning Glory | Corn | Velvet Leaf | Giant Foxtail | Barnyard Grass | Pigweed | Sorghum |
|---|---|---|---|---|---|---|---|---|---|---|---|---|---|
| (cyclohexyl)=NOC(O)N(CH₃)C(O)NH-(phenyl) | 2 | 10 | 2 | 6 | 7 | 7 | 2 | 2 | 9 | 5 | 8 | 10 | 0 |
|  | 4 | 9 | 5 | 8 | 9 | 8 | 3 | 5 | 10 | 6 | 10 | 10 | 3 |
| (cyclohexyl)=NOC(O)N(CH₃)C(O)NH-(phenyl)-Cl | 2 | 3 | 2 | 0 | 0 | 6 | 0 | 0 | 8 | 9 | 10 | 10 | 0 |
|  | 4 | 0 | 3 | 0 | 4 | 10 | 4 | 2 | 10 | 9 | 10 | 10 | 4 |
| (CH₃)₂C=NOC(O)N(CH₃)C(O)NH-(phenyl) | 2 | 1 | 5 | 2 | 10 | 10 | 9 | 6 | 10 | 8 | 6 | 10 | 2 |
|  | 4 | 3 | 6 | 5 | 10 | 10 | 10 | 7 | 10 | 9 | 9 | 10 | 5 |

TABLE 2

| Compound | Rate lb./Acre | Cotton | Sorghum | Soybeans | Barnyard Grass | Corn | Teaweed | Giant Foxtail | Pigweed | Velvet Leaf | Crabgrass | Wild Mustard | Morning Glory |
|---|---|---|---|---|---|---|---|---|---|---|---|---|---|
| (furyl)-CH=NOC(O)N(CH₃)C(O)NH-(phenyl)-Cl | 1 | 1 | 10 | 10 | 8 | 8 | 9 | 5 | 4 | 10 | 8 | 10 | 10 |
|  | 2 | 4 | 10 | 10 | 8 | 9 | 10 | 8 | 10 | 10 | 10 | 10 | 10 |
| (furyl)-CH=NOC(O)N(CH₃)C(O)NH-(phenyl)-Cl | 1 | 10 | 10 | 10 | 10 | 8 | 10 | 8 | 10 | 10 | 10 | 10 | 10 |
|  | 2 | 10 | 10 | 10 | 10 | 10 | 10 | 9 | 10 | 10 | 10 | 10 | 10 |
| (cyclohexyl)=NOC(O)N(CH₃)C(O)NH-(phenyl)-Cl | 1 | 4 | 10 | 10 | 10 | 9 | 8 | 7 | 8 | 10 | 10 | 10 | 10 |
|  | 2 | 5 | 10 | 10 | 10 | 10 | 10 | 8 | 8 | 10 | 10 | 10 | 10 |
| (phenyl)-CH=NOC(O)N(CH₃)C(O)NH-(phenyl)-Cl | 1 | 10 | 10 | 10 | 10 | 9 | 10 | 9 | 6 | 10 | 9 | 10 | 10 |
|  | 2 | 10 | 10 | 10 | 10 | 9 | 10 | 10 | 10 | 10 | 9 | 10 | 10 |

TABLE 2-continued

| Compound | Rate lb./Acre | Cotton | Sorghum | Soybeans | Barnyard Grass | Corn | Teaweed | Giant Foxtail | Pigweed | Velvet Leaf | Crabgrass | Wild Mustard | Morning Glory |
|---|---|---|---|---|---|---|---|---|---|---|---|---|---|
| 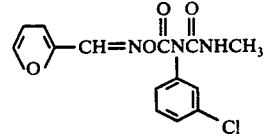 | 1<br>2 | 6<br>7 | 5<br>8 | 9<br>9 | 7<br>10 | 9<br>10 | 9<br>10 | 10<br>10 | 10<br>10 | 8<br>9 | 10<br>10 | 10<br>10 | 10<br>10 |
| 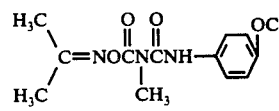 | ½<br>1 | 2<br>3 | 3<br>6 | 10<br>10 | 8<br>9 | 10<br>10 | 3<br>15 | 10<br>10 | 10<br>10 | 3<br>5 | 10<br>10 | 10<br>10 | 10<br>10 |
| 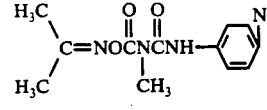 | ¼<br>½ | 0<br>1 | 5<br>6 | 3<br>5 | 3<br>7 | 4<br>6 | 2<br>4 | 3<br>6 | 2<br>3 | 3<br>4 | 3<br>4 | 3<br>4 | 8<br>10 |
| 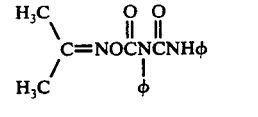 | 1<br>2 | 5<br>7 | 8<br>10 | 6<br>8 | 5<br>6 | 6<br>9 | 10<br>9 | 6<br>7 | 5<br>6 | 5<br>9 | 9<br>10 | 8<br>10 | 9<br>10 |
| 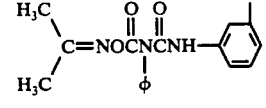 | 1<br>2 | 4<br>5 | 9<br>10 | 4<br>5 | 3<br>8 | 6<br>9 | 6<br>10 | 7<br>9 | 3<br>8 | 5<br>10 | 10<br>10 | 9<br>10 | 9<br>10 |
| 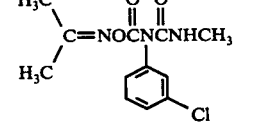 | 1<br>2 | 4<br>5 | 8<br>10 | 7<br>7 | 4<br>5 | 7<br>9 | 8<br>7 | 9<br>10 | 4<br>6 | 10<br>9 | 9<br>10 | 9<br>10 | 10<br>10 |

TABLE 3

PRE-EMERGENCE ACTIVITY COMPARISON

| Compound | Rate lbs./A | Millet | Corn | Mustard | Cotton | Soybean |
|---|---|---|---|---|---|---|
| Acetone oximinyl 2-methyl-4-phenyl allophanate | 2 | 6 | 5 | 10 | 4 | 8 |
| Acetone oxime N-phenyl carbamate | 2 | 7 | 2 | 10 | 5 | 0 |
| Isobutyraldoximinyl N-methyl carbamate | 2 | 0 | 0 | 0 | 0 | — |
| Acetone oximinyl 2-methyl-4-phenyl allophanate | 20 | 10 | 9 | 10 | 10 | 10 |
| Acetone oxime N-phenyl carbamate | 20 | 10 | 8 | 10 | 10 | 9 |
| Isobutyraldoximinyl N-methyl carbamate | 20 | 0 | 0 | 4 | 0 | — |

TABLE 4

POST-EMERGENCE ACTIVITY COMPARISON

| Compound | Rate lb./Acre | Alfalfa | Barnyard grass | Corn | Cotton | Crabgrass | Cucumber | Giant Foxtail | Morning Glory | Millet | Peas | Pigweed | Sugarbeet | Sorghum | Soybeans | Sunflower | TeaWeed | Tomato | Velvetleaf | Wheat | Wild Mustard | Wild oats |
|---|---|---|---|---|---|---|---|---|---|---|---|---|---|---|---|---|---|---|---|---|---|---|
| *1 | 2 | 3 | 6 | 6 | 1 | 10 | 10 | 9 | 9 | 3 | 1 | 10 | 6 | 2 | 2 | 9 | (1–10) | 10 | 10 | 5 | 10 | 6 |
| **2 | 2 | 10 | 3 | 2 | 0 | 9 | 3 | 6 | 0 | 5 | 0 | 9 | 8 | 0 | 0 | 0 | 9 | 4 | 9 | 0 | 10 | 0 |
| *1 | 4 | 10 | 9 | — | 3 | 10 | 10 | 9 | 10 | 6 | 2 | 10 | 8 | 5 | 5 | 9 | 10 | 10 | 10 | 6 | 10 | 7 |
| **2 | 4 | 10 | 6 | 2 | 0 | 9 | 5 | 8 | 10 | 8 | 0 | 10 | 8 | 2 | 0 | 2 | 10 | 6 | 10 | 5 | 10 | 0 |
| *1 | 8 | 10 | 10 | 8 | 5 | 10 | 10 | 10 | 10 | 10 | 5 | 10 | 10 | 8 | 8 | 10 | 10 | 10 | 10 | 10 | 10 | 7 |
| **2 | 8 | 10 | 9 | 3 | 0 | 10 | 8 | 10 | 10 | 9 | 1 | 10 | 10 | 1 | 9 | 6 | 10 | 9 | 10 | 5 | 10 | 0 |

*Acetone oximinyl 2-methyl-4-phenyl allophanate
**Actone oximinyl N-methyl carbamate

TABLE 5
POST-EMERGENCE ACTIVITY COMPARISON

| Compound | Rate lbs./A | Millet | Corn | Mustard | Cotton | Tomato | Marigold |
|---|---|---|---|---|---|---|---|
| Isobutyraldoximinyl 2-methyl-4-phenyl allophanate | 1 | 10 | 9 | 10 | 9 | 10 | 10 |
| Acetone oximinyl N-methyl carbamate | 1 | 0 | 0 | 0 | 0 | 0 | 0 |
| Isobutyraldoximinyl 2-methyl-4-phenyl-allophanate | 10 | 10 | 10 | 10 | 10 | 10 | 10 |
| Acetone oximinyl N-methyl carbamate | 10 | 0 | 3 | 5 | 2 | 0 | 1 |

What I claim and desire to protect by Letters Patent is:

1. A herbicidal composition comprising (1) application aid material and (2) an effective quantity of phytotoxic material comprising a compound of the formula:

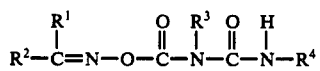

in which when $R^1$ and $R^2$ are taken separately, $R^1$ is selected independently from the group consisting of hydrogen and $C_1$-$C_7$ alkyl and $R^2$ is 2-furanyl; $R^3$ is selected from the group consisting of $C_1$-$C_7$ alkyl, allyl, phenyl, 3-halophenyl and 3,4-dihalophenyl; and $R^4$ is selected from the group consisting of $C_1$-$C_7$ alkyl, allyl, cyclohexyl, phenyl, halophenyl, tolyl, anisolyl, nitrophenyl, 3,4-dihalophenyl, 1-naphthyl, p-toluene sulfonyl, trihalomethylphenyl and 2,6-dinitro-4-trihalomethylphenyl.

2. A method for the control of weeds which comprises applying to the soil an effective quantity of material selected from the group of compounds of the formula:

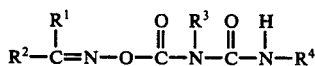

in which when $R^1$ and $R^2$ are taken separately, $R^1$ is selected independently from the group consisting of hydrogen and $C_1$-$C_7$ alkyl and $R^2$ is 2-furanyl; $R^3$ is selected from the group consisting of $C_1$-$C_7$ alkyl, allyl, phenyl, 3-halophenyl and 3,4-dihalophenyl; and $R^4$ is selected from the group consisting of $C_1$-$C_7$ alkyl, allyl, cyclohexyl, phenyl, halophenyl, tolyl, anisolyl, nitrophenyl, 3,4-dihalophenyl, 1-naphthyl, p-toluene sulfonyl, trihalomethylphenyl and 2,6-dinitro-4-trihalomethylphenyl.

3. The method according to claim 2 in which $R^1$ is hydrogen, and $R^3$ and $R^4$ are methyl.

4. A method for the control of weeds which comprises applying to the foliage of said weeds an effective quantity of material selected from the group of compounds of the formula:

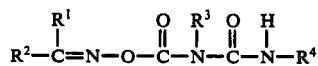

in which when $R^1$ and $R^2$ are taken separately, $R^1$ is selected independently from the group consisting of hydrogen and $C_1$-$C_7$ alkyl and $R^2$ is 2-furanyl; $R^3$ is selected from the group consisting of $C_1$-$C_7$ alkyl, allyl, phenyl, 3-halophenyl and 3,4-dihalophenyl; and $R^4$ is selected from the group consisting of $C_1$-$C_7$ alkyl, allyl, cyclohexyl, phenyl, halophenyl, tolyl, anisolyl, nitrophenyl, 3,4-dihalophenyl, 1-naphthyl, p-toluene sulfonyl, trihalomethylphenyl and 2,6-dinitro-4-trihalomethylphenyl.

5. The method according to claim 4 in which $R^1$ is hydrogen, and $R^3$ and $R^4$ are methyl.

6. A herbicidal composition according to claim 1 in which $R^1$ is hydrogen, and $R^3$ and $R^4$ are methyl.

* * * * *